(12) United States Patent  
Lang

(10) Patent No.: US 7,640,058 B2  
(45) Date of Patent: Dec. 29, 2009

(54) BIVENTRICULAR HEART STIMULATOR

(75) Inventor: Volker Lang, West Linn, OR (US)

(73) Assignee: Biotronik CRM Patent AG (CH)

( * ) Notice: Subject to any disclaimer, the term of this patent is extended or adjusted under 35 U.S.C. 154(b) by 397 days.

(21) Appl. No.: 11/537,049

(22) Filed: Sep. 29, 2006

(65) Prior Publication Data

US 2008/0082134 A1 Apr. 3, 2008

(51) Int. Cl.
*A61N 1/00* (2006.01)
(52) U.S. Cl. ...................................................... 607/17
(58) Field of Classification Search ....................... 607/9
See application file for complete search history.

(56) References Cited

U.S. PATENT DOCUMENTS

| | | | |
|---|---|---|---|
| 4,217,913 A | 8/1980 | Dutcher | |
| 6,556,866 B2 | 4/2003 | Dal Molin et al. | |
| 6,751,504 B2 | 6/2004 | Fishler | |
| 6,819,959 B1 | 11/2004 | Doan et al. | |
| 6,937,899 B2 | 8/2005 | Sheldon et al. | |
| 7,239,915 B2 * | 7/2007 | Cohen | 607/17 |
| 7,330,759 B2 * | 2/2008 | Militello | 607/17 |
| 7,440,803 B2 * | 10/2008 | Ni et al. | 607/9 |
| 2001/0012953 A1 * | 8/2001 | Molin et al. | 607/9 |
| 2003/0045805 A1 | 3/2003 | Sheldon et al. | |
| 2003/0204212 A1 * | 10/2003 | Burnes et al. | 607/17 |
| 2005/0049646 A1 | 3/2005 | Czygan et al. | |
| 2006/0079940 A1 * | 4/2006 | Ripart | 607/9 |

FOREIGN PATENT DOCUMENTS

| | | | |
|---|---|---|---|
| EP | 1 260 246 A | | 11/2002 |
| FR | 2873930 A1 * | | 2/2006 |
| WO | WO 2004050177 A1 * | | 6/2004 |
| WO | WO 2006/055202 A | | 5/2006 |

OTHER PUBLICATIONS

Search Report for European Patent Appln. No. 07017198.8, issued by the European Patent Office on Feb. 7, 2008.

* cited by examiner

*Primary Examiner*—Carl H Layno
*Assistant Examiner*—Jeremiah T Kimball
(74) *Attorney, Agent, or Firm*—Craig A. Fieschko, Esq.; DeWitt Ross & Stevens S.C.

(57) ABSTRACT

A biventricular heart stimulator is adapted to optimize an interventricular delay interval duration by minimizing a mechanical asynchrony between right and left ventricle. Mechanical asynchrony between right and left ventricle is determined by measuring right ventricular and left ventricular intracardiac impedance or conductivity.

31 Claims, 5 Drawing Sheets

BIVENTRICULAR HEART STIMULATOR

FIELD OF THE INVENTION

The invention relates to biventricular heart stimulators in general and to implantable medical devices for biventricular heart stimulation such as implantable cardiac pacemakers, implantable cardioverter/defibrillators (ICDs) or a combination thereof in particular.

Biventricular heart stimulators are used for a cardiac resynchronization therapy that shall synchronize right ventricular contraction and left ventricular contraction to improve the output of a heart exhibiting a cardiovascular disease. In particular, cardiac synchronization therapy is used to treat heart failure in patients with wide QRS complex that results from a delayed excitation of the left heart side. It is believed, that a main contributor to heart failure (the heart's inability to generate enough cardiac output) is an asynchronous mechanical contraction of the left and right side of the heart.

In order to restore an optimum cardiac output by proper synchronization of consecutive contractions of the chambers of a heart, the duration of a delay interval between a right ventricular contraction and a left ventricular contraction needs to be optimized. This delay interval is called interventricular delay or interventricular delay interval or interventricular interval and often times is abbreviated VVD.

Furthermore, in order to restore an optimum cardiac output the proper sequence of the contractions of the chambers of a heart needs to be optimized. Positive values of the VVD denote that the right ventricular chamber is stimulated first and after the WD the left ventricular. Negative values of the VVD denote that the left ventricular chamber is stimulated first, followed by the right ventricular chamber after the VVD.

In most cases a biventricular heart stimulator is able to stimulate a right atrium of the heart in addition to the right and the left ventricle. In such case, also the delay between a right atrial contraction and a right ventricular contraction needs to be optimized in order to properly synchronize right and left ventricular contraction and the right atrial contraction. The delay interval between a right atrial contraction and the right ventricular contraction usually is called atrioventricular delay interval that is abbreviated AVD.

A biventricular heart stimulator puts out an electrical stimulation pulse to a heart chamber, if no natural contraction of the heart chamber has occurred prior to expiration of a respective delay interval. In particular, a stimulation pulse to the right ventricle is triggered and delivered at the end of the atrioventricular delay interval if no natural right ventricular contraction is sensed prior to expiration of the atrial ventricular delay interval. Similarly, a stimulation pulse to the left ventricle is triggered and delivered if no left ventricular contraction is sensed prior to expiration of the interventricular delay interval.

US 2005/0131469 discloses a hemodynamic optimization system that automatically adjusts atrioventricular delay and the interventricular delay until maximum hemodynamic output is achieved. According to US 2005/0131469 hemodynamic information can be gathered via impedance measures, QT-interval, accelerometer, mixed venous oxygen duration, cardiac output or similar marker, intracardiac pressure monitoring, blood pressure, temperature and other suitable physiologic parameters. According to U.S. Pat. No. 4,303,075 the atrial ventricular delay is optimized until stroke volume reaches a maximum. Stroke volume is measured by way of an impedance processor for determining a peak to peak amplitude that corresponds to the stroke volume of the heart.

Depending on the mode of operation of the heart stimulator, triggering and delivery of stimulation pulses is inhibited if a natural contraction of a respective heart chamber is sensed prior to expiration of a respective delay interval. Thus, stimulation pulses are only triggered if needed. Such mode of operation is called demand mode.

In order to be able to operate in a demand mode, a heart stimulator comprises sensing stages for sensing natural (also called intrinsic) contractions of a respective heart chamber. A natural contraction of a heart chamber is also called an intrinsic event in contrast to a contraction of a heart chamber due to stimulation that is called a paced event. For each heart chamber to be stimulated, e.g. right atrium, right ventricle and left ventricle, a separate sensing channel is provided in order to discriminate between intrinsic events of different origin. Atrial events are usually designated with A and ventricular events are designated with V, and since the atrioventricular delay is the delay between an atrial event and a ventricular event, it is abbreviated AVD.

Further, in order to cause effective excitation of a heart chamber to be stimulated, the stimulation pulse delivered to said heart chamber needs to be strong enough to cause such excitation. Therefore, the stimulation pulse needs to have a strength above a stimulation threshold (or excitation threshold) of the heart chamber to be stimulated. On the other hand, a stimulation pulse having a strength that is much higher than the stimulation threshold would use more energy that necessary. In view of limited energy resources in an implantable medical device (IMD) unnecessary waste of energy is to be avoided to reduce battery depletion to a minimum. Therefore, modern implantable medical devices provide for automatic threshold control that continuously or periodically and automatically determines optimum stimulation pulse strength just above the stimulation threshold of a respective heart chamber.

Although the present invention is neither directed to technical details of event detection and discrimination (e.g. details of the sensing stage and the processing of signals generated by the sensing stage) nor to details of automatic capture control such features in general are incorporated in a preferred heart stimulator according to the invention. A number of solutions for intrinsic event detection and processing and for automatic capture control are unknown to the man skilled in the art.

SUMMARY OF THE INVENTION

The object to be solved by the present invention is to provide for a device and a method for optimal synchronization of a right ventricular contraction and a left ventricular contraction.

It's an object of a preferred embodiment of the invention to provide for an optimal synchronization between a right atrial contraction and a right ventricular contraction too.

According to the invention, the main object is achieved by a heart stimulation device that has at least one stimulation pulse generator for stimulating the right ventricle and the left ventricle of a heart. A control unit is connected to said stimulation pulse generator in order to trigger right ventricular stimulation pulses and left ventricular stimulation pulses and to control an interventricular delay interval (VVD) that is started with triggering of the right ventricular stimulation pulse and that will lead to triggering of a left ventricular stimulation pulse if the interventricular delay interval expires for positive VVD values. Alternatively, the interventricular delay interval (VVD) is started with triggering of the left ventricular stimulation pulse and that will lead to triggering of a right ventricular stimulation pulse if the interventricular delay interval expires for negative VVD values.

Means for determining mechanical asynchrony between right ventricular and left ventricular contraction are provided. In a preferred embodiment, mechanical asynchrony between right ventricular and left ventricular contraction is determined by means of an intracardiac impedance or conductivity measuring stage.

The intracardiac impedance or conductivity measuring stage puts out signals representing a time course of intracardiac impedance or conductivity. Two such measuring stages are provided in order to put out a right ventricular impedance or conductivity signal representing the time course of the right ventricular impedance or conductivity, respectively, and a left ventricular impedance or conductivity signal representing the time course of the left ventricular impedance or conductivity, respectively during one systole. The control unit is adapted to vary the interventricular delay interval and to determine a difference area between the time course of the right ventricular impedance or conductivity signal and the left ventricular impedance or conductivity signal for each interventricular delay duration and to determine an optimized interventricular delay interval duration that leads to a minimum of the difference area.

Preferably, both, an atrial ventricular delay interval duration (AVD) and interventricular delay interval duration are optimized.

Optimization of the atrial ventricular delay interval duration is achieved similar to interventricular delay interval duration optimization by determining the difference area for a number of different atrial ventricular delay interval duration and then determining an optimum atrial ventricular delay interval duration that is related to a minimum of the difference area.

If both, AVD and VVD, are optimized, it is preferred that the heart stimulator first optimizes AVD and then optimizes VVD while maintaining an optimum AVD.

It is to be noted that the heart stimulator according to the invention is not adapted to carry out an optimization of interventricular delay interval duration or atrioventricular delay interval duration based on finding an maximum cardiac output by way of impedance measurement. Instead, the heart stimulator according to the invention is adapted to minimize mechanical asynchrony between the right and the left ventricle of a heart. Therefore, for the heart stimulator according to the invention it is sufficient to evaluate cardiac impedance during the right ventricular and the left ventricular systole disregarding (and not even recording) any impedance or conductivity values would occur during diastole.

Since conductivity and impedance describe the same property of the subject matter, using impedance or conductivity is equivalent as far as this invention is concerned. Conductivity is the reciprocal value of the impedance. Both, intraventricular impedance or intraventricular conductivity are characteristic parameters that change during one heart cycle. The change of intraventricular impedance or intraventricular conductivity mainly depends on the volume of blood in a respective ventricle. Since blood has a lower impedance than the tissue enclosing the blood volume in a ventricle the intraventricular impedance is lower if the ventricle is filled. Therefore, a minimum impedance and a maximum conductivity is measured at the end of a diastole and a maximum impedance and a minimum conductivity is measured at the end of a systole. The term "intraventricular impedance" shall designate any measured value that mainly depends on the impedance of a blood volume in a ventricle. Similarly, "intraventricular conductivity" shall designate any conductivity that mainly depends on the blood volume in a ventricle.

If the time course of the left and the right ventricular, intracardiac impedance or conductivity is represented by a sequence of discrete values, the difference area can easily be determined by determining the absolute difference between a left ventricular impedance value and a right ventricular impedance value measured simultaneously and thus forming a pair of impedance values. If a plurality of such pairs of impedance values are generated by way of sampling, for each such pair the absolute difference may be determined and all absolute differences thus determined can be summed up. The sum thus generated represents the difference area.

Accordingly, in a preferred embodiment, the impedance or conductivity measuring stage is adapted to generate a sequence of pairs of an impedance values by way of sampling, wherein each pair of impedance values is formed by a left ventricular intracardiac impedance value and a right ventricular intracardiac impedance value measured simultaneously.

Preferably, the impedance or conductivity measuring stage is adapted to generate a sequence of sample values during one systole following the right ventricular or left ventricular excitation. The sequence may comprise 12 to 20 pairs of sample values (sampled right and left ventricular impedance values). A particularly suitable number of pairs of sample values is 16.

Since excitation of the right or left ventricle corresponds either to an intrinsic ventricular event (sensed ventricular event, Vs) or to a paced ventricular event (Vp), the impedance measuring stage can be started by any ventricular event (V), either intrinsic or paced.

Regarding details of the impedance measuring stage, it is preferred that the impedance measuring stage is adapted to inject a constant current over a pair of electrodes that also serve for measuring a voltage drop caused by said constant current. Preferably, the constant current has a strength between 100 µA and 400 µA to adapt to leads with different impedance characteristics and gain maximal resolution. A preferred duration of a single constant current pulse is between 40 and 50 µs (micro second). Injection of constant current pulses and measuring of the resulting voltage drop preferably is repeated with a sampling rate between 60 Hz and 70 Hz. An adequate period between two consecutive samples would be 16 ms. In order to avoid measuring artifacts, the constant current pulses consists of two sub-pulses with opposite sign. The impedance measuring stage filters the signals to minimize the artifacts given from breathing and body movements.

Impedance or conductivity measurement preferably is carried out via a right ventricular tip electrode and a heart stimulator's case for measuring of the right ventricular impedance or conductivity, and via a left ventricular tip electrode and the heart stimulator's case for measuring the left ventricular impedance or conductivity.

Alternatively, other available electrodes for current injection and voltage measurement may be used, like a right ventricular ring electrode or a left ventricular ring electrode or the shock coil electrode. The tip of the RV electrode and LV electrode would be used for current injection, and the voltage measurement would be done between the tip of the TV and LV lead versus the ring of the RV or LV, or versus the shock coil.

In a further preferred embodiment, the heart stimulator comprises a sensor for measuring the physical load, the sensor being an acceleration sensor that is connected to the control unit and which allows for optimization of AVD and VVD for different load conditions of a patient, such as rest and load. According to this embodiment, an optimum AVD and an optimum VVD that are determined under rest, when the activity sensor indicates no physical or low physical activity of a patient, are stored separately from a different optimum AVD and VVD duration that are determined under load, that is, when the physical load sensor indicates increased activity of the patient. According to this embodiment, the heart stimulator is adapted to store an optimum VVD that is to be applied for biventricular stimulation when the activity sensor indicates no or low activity, and another optimal VVD duration that is to be applied when the activity sensor indicates increased activity of the patient. Similarly, a preferred heart stimulator would store two different optimum values of AVD duration that are to be applied under rest or under load respectively. Based on the stored optimum values and the actual signal from the activity sensor, the optimal AVD and VVD are interpolated between the optimum values for rest and activity conditions.

In a further preferred embodiment, the heart stimulator comprises a sensor for measuring the physical load via impedance, the sensor being connected to the control unit and allowing for optimization of AVD and VVD for different load conditions of a patient, such as rest and load. According to this embodiment, an optimum AVD and an optimum VVD that are determined under rest, when the impedance sensor indicates no physical activity of a patient, are stored separately from a different optimum AVD and VVD duration that are determined under load, that is, when the impedance sensor indicates increased load of the patient. According to this embodiment, the heart stimulator is adapted to store an optimum VVD that is to be applied for biventricular stimulation when the activity sensor indicates no or low activity, and another optimal VVD duration that is to be applied when the activity sensor indicates increased activity of the patient. Similarly, a preferred heart stimulator would store two different optimum values of AVD duration that are to be applied under rest or under load respectively. Based on the stored optimum values and the actual load signal from the impedance sensor, the optimal AVD and VVD are interpolated between the optimum values for rest and load conditions.

In such embodiment, an activity sensor that is usually provided in a rate adaptive pace maker in order to adapt a pacing rate to a hemodynamic demand of a patient that increases with increased activity of the patient and that decreases with decreased activity of the patient can also be used to first determine and to later select an optimum VVD duration and/or an optimum AVD duration depending on the patient's physical activity.

With respect to AVD duration and VVD duration optimizing and storing of optimum AVD and VVD values, it is preferred to repeat AVD duration optimization and/or VVD duration optimization every 72 to 168 hours that is every third day or every seventh day, respectively.

The object of the invention is also achieved by a method for optimizing an atrioventricular delay interval (AVD) duration and an interventricular delay interval (VVD) duration in a three chamber biventricular heart stimulation device. Said method comprises the steps of:

Measuring right ventricular impedance or conductivity and left ventricular impedance or conductivity simultaneously.

Determining an amount of mechanical asynchrony by calculating an absolute area enclosed between the simultaneously measured right ventricular impedance or conductivity values and left ventricular impedance or conductivity values.

Varying the atrioventricular delay interval duration while maintaining fixed interventricular delay interval duration and determining said amount of mechanical asynchrony for each atrioventricular delay interval duration Determining an optimum atrioventricular delay interval duration that leads to a minimum amount of mechanical asynchrony, Varying the interventricular delay interval duration from negative values (LV to RV stimulation) to positive values (RV to LV stimulation) while maintaining a fixed atrioventricular delay interval duration, said fixed atrioventricular delay interval duration being the optimum atrioventricular delay interval duration and determining said amount of mechanical asynchrony for each interventricular delay interval duration Determining an optimum interventricular delay interval duration that leads to a minimum amount of mechanical asynchrony.

For the purpose of the present invention, the time course of right ventricular, intracardiac impedance and left ventricular intracardiac impedance is measured in order to determine a difference area that corresponds to a time delay between the time course of the right ventricular intracardiac impedance and the left ventricular intracardiac impedance during a systole.

In an alternative embodiment, such time delay of mechanical contraction between the right ventricle and left ventricle can be determined by using a right ventricular acceleration sensor placed at the distal end of a right ventricular electrode lead and a left ventricular acceleration sensor placed at the distal end of a left ventricular electrode lead. In a preferred embodiment of the alternative embodiment, VVD and/or AVD are optimized in order to achieve minimum delay between the maximum value of right ventricular acceleration sensor output signal (50-300 ms after the right ventricular event) and the maximum value of left ventricular acceleration sensor output signal (50-300 ms after the left ventricular event).

In an alternative embodiment, such time delay of mechanical contraction between the right ventricle and left ventricle can be determined by using a right ventricular echo sensor placed at the distal end of a right ventricular electrode lead and a left ventricular echo sensor placed at the distal end of a left ventricular electrode lead. In a preferred embodiment of the alternative embodiment, VVD and/or AVD are optimized in order to achieve minimum delay between the maximum value of right Echo sensor output signal (50-300 ms after the right ventricular event) and the maximum value of left ventricular echo sensor output signal (50-300 ms after the left ventricular event).

BRIEF DESCRIPTION OF THE DRAWINGS

The foregoing and other objects, advantages and novel features of the present invention can be understood and appreciated by reference to the following detailed description of the invention, taken in conjunction the accompanying drawings, in which.

DESCRIPTION OF PREFERRED VERSIONS OF THE INVENTION

Figure 1:
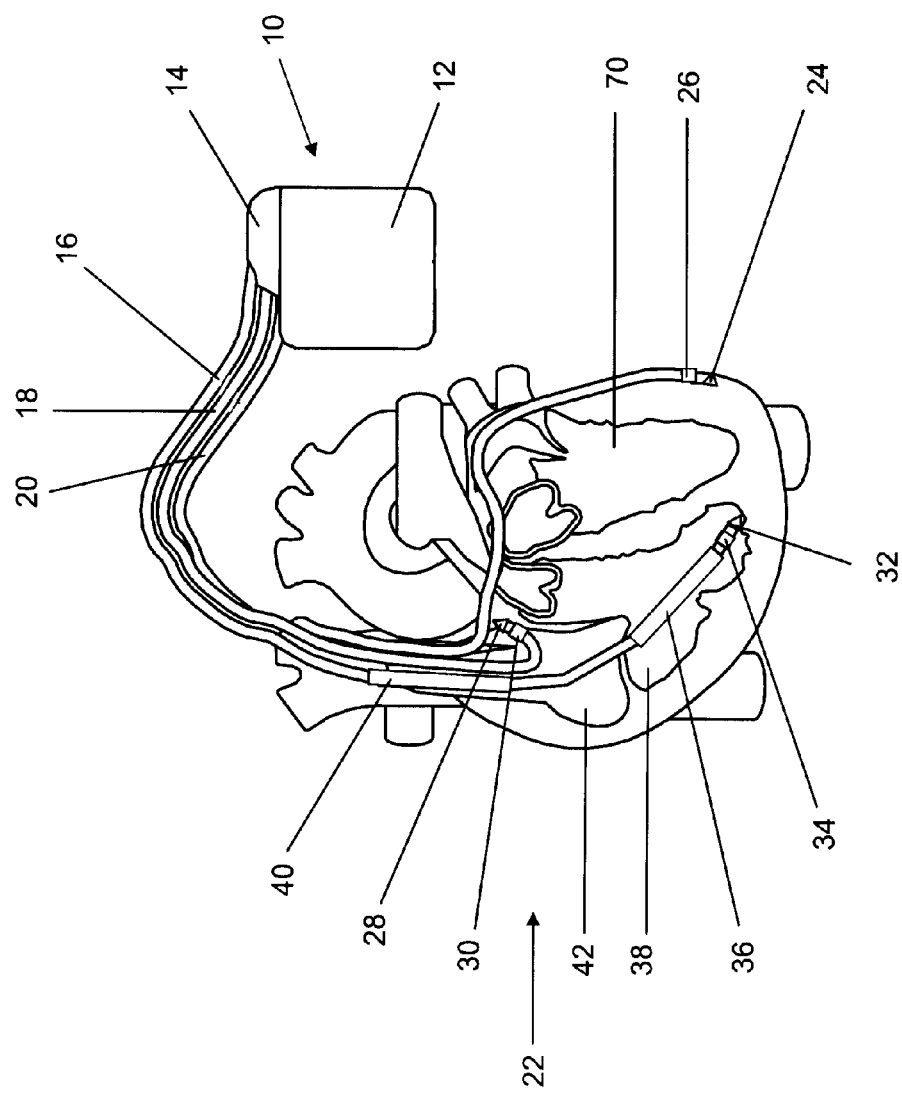
FIG. 1 illustrates the heart stimulator connected to electrode leads that are placed in a heart.

From FIG. 1 it is apparent that stimulator 10 comprises a case 12 and header 14.

The heart stimulator 10 is connected to three electrode leads, namely a right ventricular electrode lead for 16, a right atrial electrode lead 18 and a left ventricular electrode lead 20.

The left ventricular electrode lead 20 is designed to pass trough the coronary sinus of heart 22. A typical electrode suitable for use with heart stimulator 10 is the electrode lead Corox+ UP/BB by the applicant. Left ventricular electrode lead 20 comprises a left ventricular tip electrode 24 at the distal end a left ventricular electrode lead 20 and a left ventricular ring electrode 26.

Atrial electrode lead 18 comprises a right atrial tip electrode 28 at the distal end of right atrial electrode lead 18 and a right atrial ring electrode 30.

The right ventricular electrode lead 16 comprises right ventricular tip electrode 32 at the distal end of right ventricular electrode lead 16 and a right ventricular ring electrode 34.

In order to illustrate that heart stimulator 10 may be adapted to act as an implantable cardioverter/defibrillator (ICD) ventricular electrode lead 16 also exhibits a ventricular shock coil 36 for the delivery of defibrillation shocks to right ventricle 38 of heart 22 and an atrial shock coil 40 for the delivery of atrial defibrillation shocks to a right atrium 42 of heart 22.

Each electrode and shock coil of electrode leads 16 to 20 is separately connected to an electric circuit enclosed by case 12 of heart stimulator 10 by way of electrical contacts of a plug (not shown) at the proximal end of each electrode lead 16 to 20 and corresponding contacts (not shown) in header 14 of heart stimulator 10.

Figure 2:
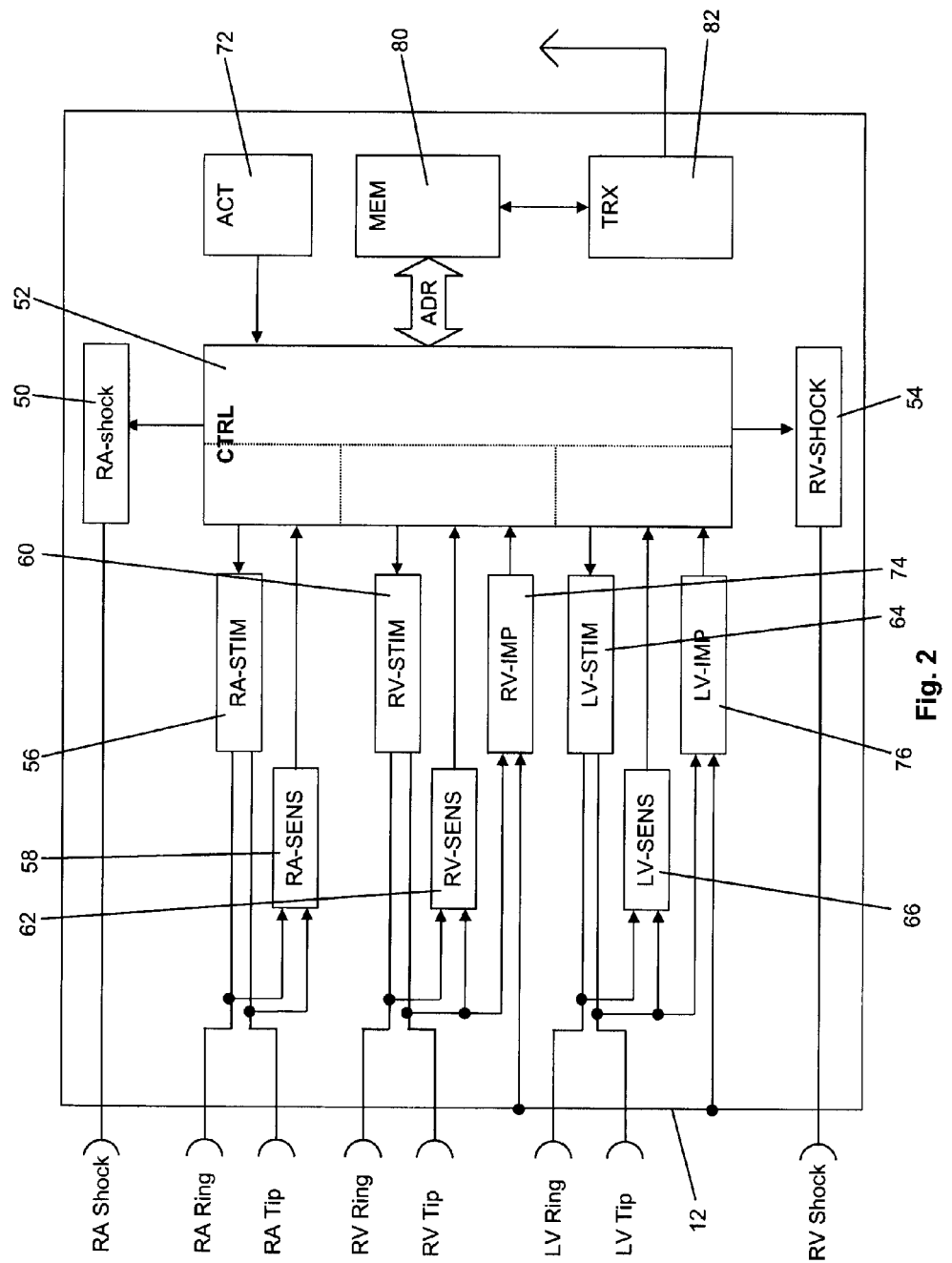
FIG. 2 shows a schematic block diagram of the heart stimulator of FIG. 1.

Right atrial shock coil 40 is connected to right atrial shock generator 50 (see FIG. 2) that is controlled by a control unit 52 of heart stimulator 10.

Similarly, right ventricular shock coil 36 is connected to a right ventricular shock generator 54 that is also connected to control unit 52.

Right atrial tip electrode 28 and right atrial ring electrode 30 are both connected to a right atrial stimulation pulse generator 56 and a right atrial sensing stage 58 that internal both connected to control unit 52.

Right atrial stimulation pulse generator 56 is adapted to generate atrial stimulation pulses of sufficient strength to cause an excitation of atrial myocardium by an electrical pulse delivered via right atrial tip electrode 28 and right atrial ring electrode 30. Preferably, means are provided to adapt the right atrial stimulation pulse strength to the stimulation threshold in the right atrium.

Right atrial sensing stage 58 is adapted to pick up myocardial potentials indicating an intrinsic atrial excitation that corresponds to a natural atrial contraction. By way of right atrial sensing stage 58, it is possible to stimulate the right atrium 42 of heart 22 in a demand mode wherein a right atrial stimulation pulse is inhibited if an intrinsic atrial event (intrinsic atrial excitation) is sensed by right atrial sensing stage 58 prior to expiration of an atrial escape interval.

In a similar manner, right ventricular ring electrode 34 and right ventricular tip electrode 32 are connected to right ventricular stimulation pulse generator 60 and to a right ventricular sensing stage 62 that in turn are connected to control unit 52. By way of right ventricular tip electrode 32, right ventricular ring electrode 34, right ventricular stimulation generator 60 and right ventricular sensing stage 62, right ventricular stimulation pulses can be delivered in a demand mode to the right ventricle 38 of heart 22.

In the same way left ventricular tip electrode 32 and left ventricular ring electrode 26 are connected to the left ventricular stimulation pulse generator 64 and the left ventricular sensing stage 66 that internal connected to control unit 52 and that allow for stimulating a left ventricle 70 of heart 22.

Triggering and inhibition of delivery of stimulation pulses to the right atrium, the right ventricle or the left ventricle is controlled by control unit 52, in a manner known to the man skilled in the art. The timing that schedules delivery of stimulation pulses if needed is controlled by a number of intervals, that at least partly may depend on a hemodynamic demand of a patient that is sensed by means of an activity sensor 72 that is connected to control unit 52. Activity sensor 72 allows for rate adaptive pacing wherein a pacing rate (the rate of consecutive ventricular stimulation pulses for a duration of consecutive atrial stimulation pulses) depends on a physiological demand of a patient that is sensed by a way of activity sensor 72. Details of rate adaptation are known to the man skilled in the art but need not to be explained in detail in this description.

Whereas an actual stimulation rate determines the timing from one (paced) heart cycle to another, intervals like the atrioventricular delay interval and the interventricular delay interval determine the timing within one heart cycle. Starting with an atrial event, the right ventricle would be excited (either intrinsically or paced) at the end of the atrioventricular delay interval. A left ventricular contraction should follow the right ventricular contraction at the end of the interventricular delay interval. This shall include the case, wherein the right ventricle and the left ventricle are excited the same time resulting in an interventricular delay interval duration of zero. Also, it is possible that the left ventricle is excited prior to the right ventricle resulting in a negative interventricular delay interval duration.

In any case, the atrial ventricular delay interval duration and the interventricular delay interval duration need to be adapted to an individual heart in order to achieve an optimized cardiac output.

Heart stimulator 10 is adapted to determine an optimal atrioventricular delay interval duration and an optimal interventricular delay interval duration automatically. This is achieved by finding that atrioventricular interval and that interventricular interval that leads to minimum mechanical asynchrony between the right ventricular contraction and the corresponding left ventricular contraction.

For this purpose, heart stimulator 10 comprises a right ventricular impedance measuring stage 74 and the left ventricular impedance measuring stage 76.

The right ventricular impedance measuring stage 74 and the left ventricular impedance measuring stage 76 are adapted to simultaneously measure the time course of right ventricular impedance and left ventricular impedance, respectively, by way of sampling.

Impedance measurement by impedance measuring stages 74 and 76 is started by control unit 52 either in synchrony with a right ventricular event or a left ventricular event, whatever comes first. A paced ventricular event corresponds to triggering any of the two ventricular stimulation pulse generators by control unit 52. A sensed ventricular event occurs, if one of ventricular sensing stages 62 or 66 records an intrinsic ventricular excitation.

Impedance measurement of right ventricular impedance measuring stage 74 is carried out by injecting a sequence of 16 constant current pulses of alternating voltage via right ventricular tip electrode 32 and the heart stimulator's case 12. Each constant current pulse has a same strength between 100 µA and 400 µA. The voltage drop caused by each constant current pulse is measured via the same two electrodes, e.g. right ventricular tip electrode and case 32. Each voltage drop thus measured corresponds to a momentary right ventricular intracardiac impedance. The total sequence of 16 voltage samples represents the time course of the right ventricular intracardiac impedance. The time period between two samples is 16 ms corresponding to a sampling rate of 62.5 Hz.

In a similar manner, the time course of left ventricular impedance is sampled by left ventricular impedance measuring stage 76 via left ventricular tip electrode 24 and heart stimulator's case 12.

Two voltage samples (representing a right ventricular impedance and a left ventricular impedance, respectively) measured at the same time form one pair of sample values. Thus, a total number of 16 pairs of sample values are obtained.

In order to determine mechanical asynchrony between the right ventricle and the left ventricle, for each pair of sample values the absolute difference between a voltage drop measured by the right ventricular impedance measuring stage 74 and the voltage drop measured by the left ventricular impedance measuring stage 76 is calculated. Thereafter, all 16 absolute differences thus determined are summed up. The sum thus obtained represents the absolute difference area AA between the time courses of the right ventricular intracardiac impedance and the left ventricular intracardiac impedance.

Figure 3:
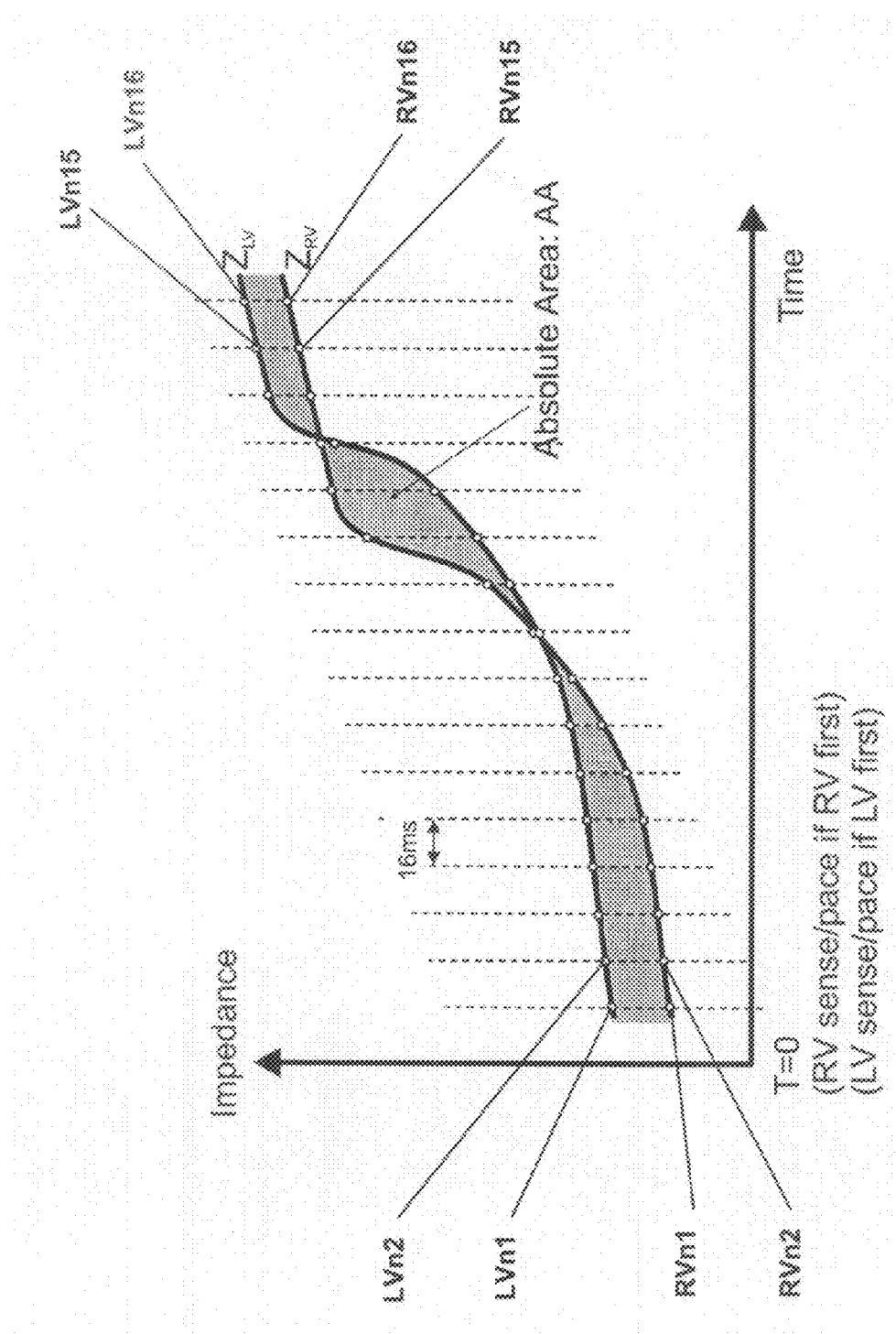
FIG. 3 is a graphical representation of a typical time course of a right and left ventricular impedance during systole.
Figure 4A:
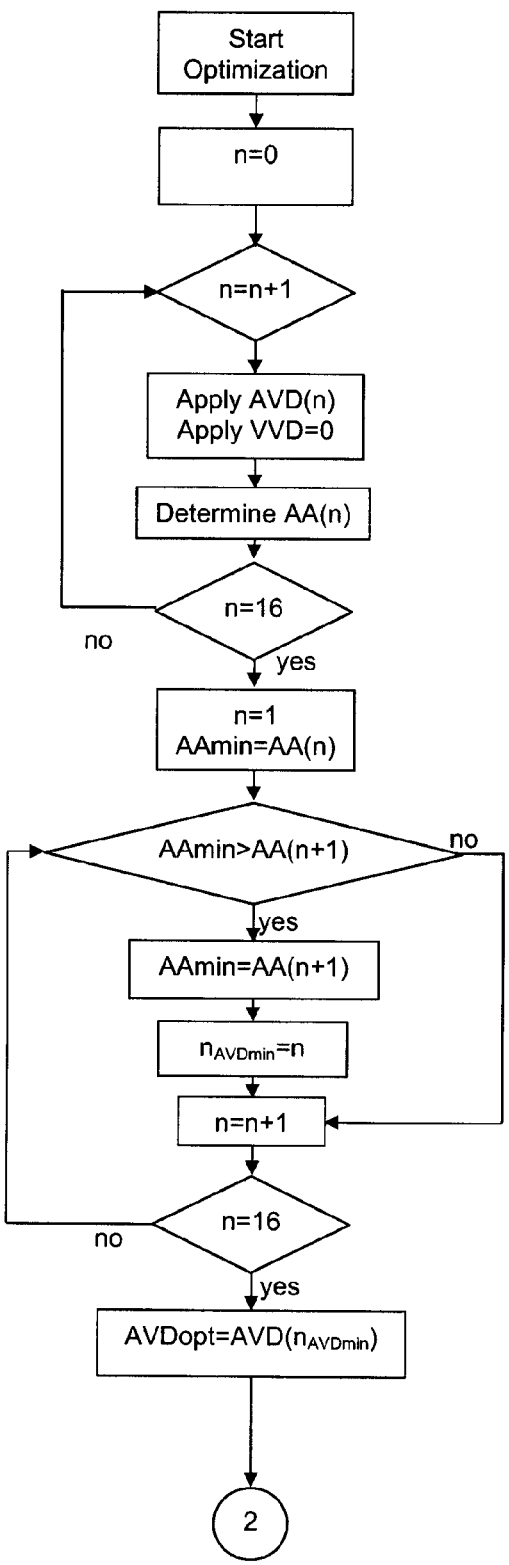
FIG. 4 is a flow chart illustrating the operation of the heart stimulator of FIG. 2.
Figure 4B:
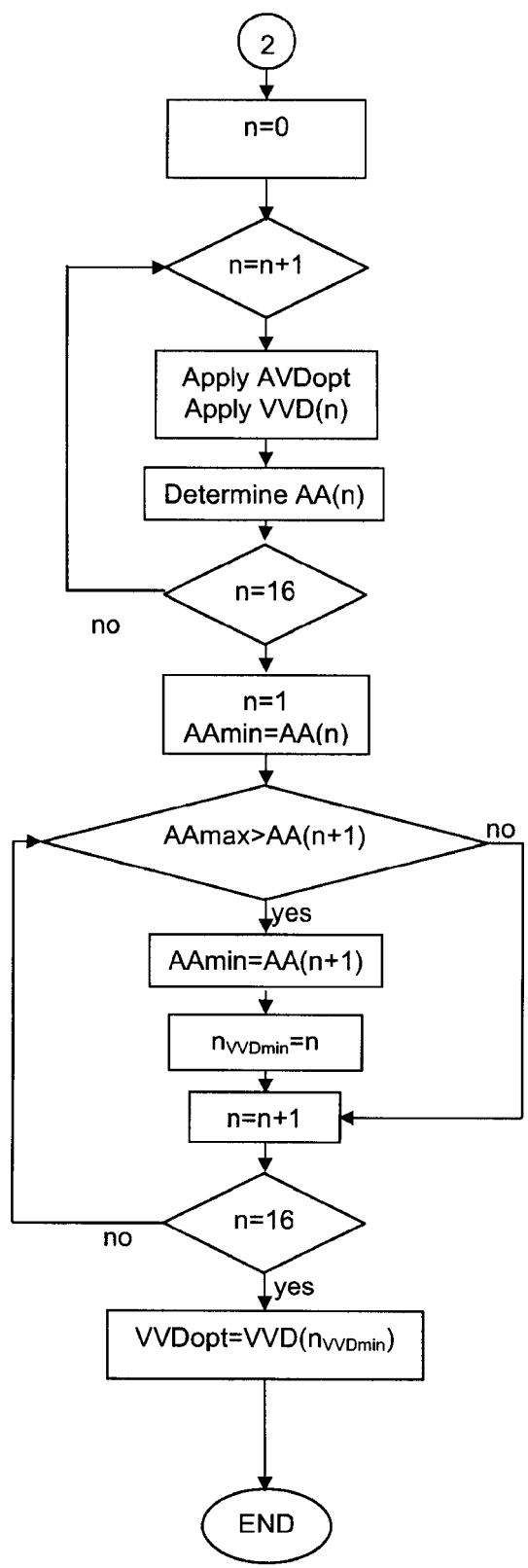

In order to illustrate the difference area, in FIG. 3 a typical time course of the right ventricular impedance $Z_{RV}$ and the left ventricular intracardiac impedance $Z_{LV}$ is graphically represented by a continuous line each. The area enclosed between these two lines is the absolute difference area (absolute area; AA). The absolute difference area AA is marked by grey shading (hatching) in FIG. 3.

In order to illustrate sampling of impedance values, the sixteen exemplary samples RVn1 to RVn16 taken by right ventricular impedance measuring stage 74 and the sixteen samples LVn1 to LVn16 taken by left ventricular impedance measuring stage 76 are marked in FIG. 3. Taking these sixteen right ventricular impedance samples RVn1 to RVn16 and sixteen left ventricular impedance samples LVn1 to LVn16, the absolute difference area AA representing the mechanical asynchrony between the right ventricle and the left ventricle can be calculated as follows:

$$AA = abs(RVn1-LVn1) + \ldots + abs(RVn16-LVn16).$$

Control unit 52 is adapted to optimize the atrioventricular delay interval duration and the interventricular delay interval duration by finding an atrioventricular delay interval duration and an interventricular delay interval duration that leads to a minimum AA. First, control unit 52 applies a number of different atrioventricular delay interval durations while maintaining an interventricular delay interval duration of 0 and determines the absolute difference area AA for each atrioventricular delay interval duration (AVD) thus tested. A total number of 8 atrioventricular delay interval durations between 50 to 450 ms is tested (50 ms, 100 ms, 150 ms, 200 ms, 300 ms, 350 ms, 400 ms, 450 ms). Then, the atrioventricular delay interval duration AVD leading to a minimum absolute difference area AA is maintained while testing a number of interventricular delay interval durations between minus 70 ms and plus 70 ms in 5 to 10 ms steps.

The algorithm for determining an optimum atrioventricular delay interval and an optimum interventricular delay interval can be summed up as follows:

```
calculate Mechanical_asynchrony_measure = abs(RVn1-LVn1) + ... +
abs(RVn16-LVn16)
find minmal sum for varying AV-delay and VV-delay:
Min(Mechanical_asynchrony_measure, for all AVD, for all VVD)
    keep VV delay at 0 ms and vary AVD from 50 to 450 ms in 50 ms step
    for minimal Mechanical_asynchrony_measure of all AVD
        keep AVD and vary VV delay from -70 ms to +70 ms in 5 to 10 ms
        step
        find minimal Mechanical_asynchrony_measure
```

This algorithm is rerun every 3 to 7 days. Preferably, the algorithm (optimization cycle) is run twice, one time when the patient is at rest and the other time when the patient exhibits physical activity. The state of rest and the state of physical activity is determined by the activity sensor 72 or by the impedance sensor 74. Thus, a total of four optimal delay interval durations is obtained, namely optimum atrioventricular delay interval duration at rest, an optimum atrioventricular delay interval duration under load, an optimum interventricular delay interval duration at rest, and an optimum interventricular delay interval duration under load. These four values are stored in a memory 80 of heart stimulator 10.

Also, a minimum absolute difference area achieved when applying the optimum atrioventricular delay interval duration and the optimum interventricular delay interval duration is stored in memory 80 so it can be transmitted telemetrically to home monitoring service center via transceiver 82.

In addition, it is preferred that the impedance signal from RV and LV in real-time is transmitted to a programmer in order to enable a physician to review the process of automatic optimization of VVD and AVD during follow-up scenarios.

What is claimed is:
1. A heart stimulator comprising:
   a. at least one stimulation pulse generator being connected to or being connectable to a right ventricular stimulation electrode lead and a left ventricular electrode lead and being adapted to generate right ventricular stimulation pulses and left ventricular stimulation pulses,
   b. a control unit connected to the stimulation pulse generator and being adapted to trigger right ventricular stimulation pulses and left ventricular stimulation pulses, wherein:
      (1) a left ventricular stimulation pulse follows a right ventricular stimulation pulse after expiration of a positive interventricular delay interval (VVD) that is started with triggering of a right ventricular stimulation pulse, or
      (2) a right ventricular stimulation pulse following a left ventricular stimulation pulse after expiration of a negative interventricular delay interval (VVD) that is started with triggering of a left ventricular stimulation pulse,
      the interventricular delay interval being adjustable,
   c. an intracardiac impedance or conductivity measuring stage being connected to the control unit and being adapted to put out a time varying signal corresponding to the intracardiac impedance or conductivity, wherein the intracardiac impedance or conductivity measuring stage is adapted to generate a right ventricular impedance signal representing the right ventricular impedance or conductivity and a left ventricular impedance signal representing the left ventricular impedance or conductivity, wherein the control unit is adapted to
(1) vary the interventricular delay interval,
(2) determine a difference area between the right ventricular impedance signal and the left ventricular impedance signal for each interventricular delay interval duration, and
(3) determine an optimized interventricular delay interval duration leading to a minimum of the difference area.

2. The heart stimulator of claim 1:
   a. having a stimulation pulse generator being connected to or being connectable to a right atrial stimulation electrode lead and being adapted to generate right atrial stimulation pulses that can be triggered by the control unit,
   b. wherein the control unit is adapted to:
      (1) vary an atrioventricular delay interval AV between a right atrial stimulation pulse and a right ventricular stimulation pulse while maintaining a fixed interventricular delay interval duration, and
      (2) determine an optimized atrioventricular delay interval duration leading to a minimum of the difference area.

3. The heart stimulator of claim 1 wherein the control unit is adapted to:
   a. first determine an optimized atrioventricular delay interval duration, and then to
   b. determine an optimized interventricular delay interval duration while maintaining the optimized atrioventricular delay interval duration.

4. The heart stimulator of claim 1 wherein the intracardiac impedance measuring stage is adapted to measure impedance via two electrodes that serve for current injection and voltage measurement.

5. The heart stimulator of claim 4 wherein the intracardiac impedance or conductivity measuring stage is adapted to measure the right ventricular impedance or conductivity signal by means of a first electrode being a heart stimulator's case and a second electrode being a right ventricular tip electrode.

6. The heart stimulator of claim 4 wherein the intracardiac impedance or conductivity measuring stage is adapted to measure the left ventricular impedance or conductivity signal by means of a first electrode being a heart stimulator's case and a second electrode being a left ventricular tip electrode.

7. The heart stimulator of claim 1 wherein the intracardiac impedance or conductivity measuring stage is adapted to generate the right ventricular impedance or conductivity signal and the left ventricular impedance or conductivity signal separately and simultaneously.

8. The heart stimulator of claim 1 wherein the intracardiac impedance or conductivity measuring stage is adapted to generate the right ventricular impedance or conductivity signal and the left ventricular impedance or conductivity signal by sampling the right ventricular impedance or conductivity and the left ventricular impedance or conductivity with a sampling rate.

9. The heart stimulator of claim 8 wherein the sampling rate is between 60 Hz and 70 Hz.

10. The heart stimulator of claim 8 wherein the intracardiac impedance or conductivity measuring stage is adapted to generate a sequence of right and left ventricular impedance or conductivity sample values, the sequence being started with a right ventricular or a left ventricular event.

11. The heart stimulator of claim 10 wherein the sequence consists of 12 to 20 pairs of sample values, each pair of sample values comprising one right ventricular impedance or conductivity sample value and one left ventricular impedance or conductivity sample value that are measured simultaneously.

12. The heart stimulator of claim 8 wherein the intracardiac impedance or conductivity measuring stage is adapted to:
    a. generate one impedance or conductivity sample value by delivering an excitation current pulse of a strength between 100 microA and 400 microA and a duration between 0.03 ms and 0.05 ms, and
    b. measure a voltage caused by the excitation current pulse.

13. The heart stimulator of claim 12 wherein the intracardiac impedance or conductivity measuring stage is adapted to generate a sequence of excitation current pulses wherein consecutive excitation current pulses have an alternating polarity.

14. The heart stimulator of claim 1 wherein the control unit is adapted to determine the difference area by calculating an absolute area difference between RV and LV impedance curves.

15. The heart stimulator of claim 14 wherein the control unit is adapted to determine the difference area by:
    a. determining for each pair of sample values of the sequence an absolute difference between the right ventricular impedance or conductivity sample value and the left ventricular impedance or conductivity sample value of the pair, and
    b. summing the absolute differences thus determined over one sequence of sample values.

16. The heart stimulator of claim 1 wherein the control unit is connected to a memory for storing an optimum interventricular delay interval (VVD) duration and/or an optimum atrioventricular delay interval (AVD) duration.

17. The heart stimulator of claim 16 wherein the control unit is adapted to:
    a. determine an optimum interventricular delay interval (VVD) duration and/or an optimum atrioventricular delay interval (AVD) duration during an optimization cycle that is repeated every 3 to 7 days, and
    b. store an optimum interventricular delay interval (VVD) duration and/or an optimum atrioventricular delay interval (AVD) duration determined during the optimization cycle,
    so that the stored optimum interventricular delay interval (VVD) duration and/or the stored optimum atrioventricular delay interval (AVD) duration can be applied for pacing in time periods following an optimization cycle.

18. The heart stimulator of claim 17 comprising a sensor for measuring the load that is connected to the control unit, wherein the control unit is adapted to run at least two different optimization cycles, one optimization cycle being carried out when the activity sensor indicates a state of rest and another optimization cycle when the sensor for measuring the load indicates a state of activity, to thus obtain two different optimum interventricular delay interval (VVD) durations and/or two different optimum atrioventricular delay interval (AVD) durations, one optimum interventricular delay interval (VVD) duration and/or optimum atrioventricular delay interval (AVD) duration to be applied in time periods following the optimization cycle when the sensor for measuring the load indicates a state of rest and the other optimum interventricular delay interval (VVD) duration and/or optimum atrioventricular delay interval (AVD) duration to be applied in time periods following the optimization cycle when the sensor for measuring the load indicates a state of activity.

19. The heart stimulator of claim 1 wherein the control unit is connected to a telemetric transmitter for transmitting an minimum value of the difference area obtained when applying the optimum interventricular delay interval (VVD) duration and/or optimum atrioventricular delay interval (AVD) duration to an external device.

20. A method for optimizing an atrioventricular delay interval (AVD) duration and an interventricular delay interval (VVD) duration in a heart stimulation device, the method comprising the steps of:
   a. measuring right ventricular impedance or conductivity and left ventricular impedance or conductivity simultaneously;
   b. determining an amount of mechanical asynchrony by calculating an absolute area enclosed between the simultaneously measured right ventricular impedance or conductivity values and left ventricular impedance or conductivity values;
   c. varying the atrioventricular delay interval duration while maintaining a fixed interventricular delay interval duration and determining the amount of mechanical asynchrony for each atrioventricular delay interval duration;
   d. determining an optimum atrioventricular delay interval duration that leads to a minimum amount of mechanical asynchrony;
   e. varying the interventricular delay interval duration while maintaining a fixed atrioventricular delay interval duration, the fixed atrioventricular delay interval duration being the optimum atrioventricular delay interval duration;
   f. determining the amount of mechanical asynchrony for each interventricular delay interval duration;
   g. determining an optimum interventricular delay interval duration that leads to a minimum amount of mechanical asynchrony.

21. The method of claim 20 wherein the right ventricular impedance or conductivity is measured between a right ventricular tip electrode and a case of the heart stimulation device.

22. The method of claim 20 wherein the left ventricular impedance or conductivity is measured between a left ventricular tip electrode and a case of the heart stimulation device.

23. The heart stimulator of claim 1 wherein:
   a. the right ventricular impedance signal represents the time interval of the right ventricular impedance or conductivity, and
   b. the left ventricular impedance signal represents the time interval of the left ventricular impedance or conductivity,
during the systole starting after the first triggered ventricular stimulation pulse.

24. A heart stimulator including:
   a. at least one stimulation pulse generator being connected to or being connectable to a right ventricular stimulation electrode lead and a left ventricular electrode lead and being adapted to generate right ventricular stimulation pulses and left ventricular stimulation pulses,
   b. a control unit connected to the stimulation pulse generator and being adapted to trigger right ventricular stimulation pulses and left ventricular stimulation pulses wherein:
      (1) a left ventricular stimulation pulse follows a right ventricular stimulation pulse after expiry of a positive interventricular delay interval (VVD) that is started with triggering of a right ventricular stimulation pulse, or
      (2) a right ventricular stimulation pulse follows a left ventricular stimulation pulse after expiry of a negative interventricular delay interval (VVD) that is started with triggering of a left ventricular stimulation pulse,
the interventricular delay interval being adjustable,
   c. sensors providing time varying signals corresponding to:
      (1) the degree of mechanical contraction in the right ventricle, and
      (2) the degree of mechanical contraction in the left ventricle,
   wherein the control unit is adapted to
      (1) vary the interventricular delay interval via the stimulation pulse generator,
      (2) determine a difference area between the time varying signals of the right and left ventricles for each interventricular delay interval duration, and
      (3) determine an interventricular delay interval leading to a reduction of the difference area.

25. A heart stimulator including:
   a. a stimulation pulse generator providing right ventricular stimulation pulses and left ventricular stimulation pulses,
   b. a control unit in communication with the stimulation pulse generator and triggering the right ventricular stimulation pulses and left ventricular stimulation pulses, wherein the right ventricular stimulation pulses and left ventricular stimulation pulses are spaced in time by an interventricular delay interval;
   c. sensors communicating time varying signals to the control unit, the time varying signals corresponding to:
      (1) the degree of mechanical contraction in the right ventricle, and
      (2) the degree of mechanical contraction in the left ventricle,
   wherein the control unit is adapted to
      (1) vary the interventricular delay interval,
      (2) determine a difference area between the time varying signals of the right and left ventricles for each interventricular delay interval, and
      (3) adapt the interventricular delay interval to reduce the difference area.

26. The heart stimulator of claim 25 wherein the time varying signals corresponding to:
   a. the degree of mechanical contraction in the right ventricle, and
   b. the degree of mechanical contraction in the left ventricle,
   correspond to the degree of mechanical contraction during the systole starting after the first triggered ventricular stimulation pulse.

27. The heart stimulator of claim 1 wherein the right ventricular impedance or conductivity signal and the left ventricular impedance or conductivity signal are generated only during the systole.

28. The method of claim 20 wherein the right ventricular impedance or conductivity and left ventricular impedance or conductivity are only measured during the systole.

29. The method of claim 20 wherein the amount of mechanical asynchrony is determined by calculating an absolute area enclosed between the simultaneously measured right ventricular impedance or conductivity values and left ventricular impedance or conductivity values during the right ventricular and left ventricular systole.

30. The heart stimulator of claim 24 wherein the time varying signals are only provided by the sensors over a time period at least substantially corresponding to the systole.

31. The heart stimulator of claim 25 wherein the time varying signals are only communicated by the sensors over a time period at least substantially corresponding to the systole.

* * * * *